United States Patent [19]

Bardenheuer et al.

[11] 4,148,221
[45] Apr. 10, 1979

[54] APPARATUS FOR SAMPLING MOLTEN METAL

[75] Inventors: Friedrich Bardenheuer, Krefeld; Gustav Kolb, Garbeck, both of Fed. Rep. of Germany

[73] Assignees: Mannesmann Aktiengesellschaft, Dusseldorf; Gustav Kolb, Garbeck, both of Fed. Rep. of Germany

[21] Appl. No.: 905,992

[22] Filed: May 15, 1978

[30] Foreign Application Priority Data

Aug. 25, 1977 [DE] Fed. Rep. of Germany ....... 2738568

[51] Int. Cl.² ............................................. G01N 1/12
[52] U.S. Cl. ............................................. 73/425.4 R
[58] Field of Search ..................... 73/425.4 R, DIG. 9

[56] References Cited

U.S. PATENT DOCUMENTS

| 4,007,640 | 2/1977 | Boron ............... 73/DIG. 9 |
| 4,010,649 | 3/1977 | Falk ................. 73/DIG. 9 |
| 4,046,016 | 9/1977 | Hackett ............ 73/425.4 R |
| 4,048,857 | 9/1977 | Bardenheuer ........... 73/354 |
| 4,102,197 | 7/1978 | Bardenheuer ...... 73/425.4 R |

*Primary Examiner*—S. Clement Swisher
*Attorney, Agent, or Firm*—Smyth, Pavitt, Siegemund, Jones & Martella

[57] ABSTRACT

A ceramic body has an inlet duct, a mixing chamber for mixing the sampled steel with a steel killing agent; an outlet duct beginning next to the inlet duct port in the lower half of the mixing chamber, leads to a sampling chamber for a pin-shaped sample and is, in turn, connected to a vented chamber for a disk sample.

12 Claims, 2 Drawing Figures

APPARATUS FOR SAMPLING MOLTEN METAL

BACKGROUND OF THE INVENTION

The present invention relates to an apparatus for sampling molten metal.

It is known to sample a bath of molten metal for purposes of analyzing its content. For this purpose a sampling device has been used having two joined half shells made of refractory ceramic material and having cavities for receiving the samples. The half shells are interconnected by means of a tube. Preferably, this tube is made of cardboard and is used for handling the sampling device, particularly for submerging the device into the metal bath and for removing a sample therefrom.

An example of such a device is described in German Offenlegungsschrift No. 25 19 957. Conventionally, pin-shaped and disk-shaped samples are obtained by such a device. Another such sampling device is described by us in U.S. Pat. No. 4,048,857 issued Sept. 20, 1977. Upon sampling molten steel, particularly from a converter holding unkilled steel, it is necessary to quiet the steel in the sampling device by an agent binding oxygen, preferably aluminum. In addition, it is required that the agent for killing the steel in the obtained sample be extremely uniformly distributed so that errors are avoided in the spectrum analysis test conducted at a later time.

The known sampling devices do not satisfy the present day high quality requirements.

SUMMARY OF THE INVENTION

It is an object of the present invention to improve the quality of samples obtained from molten metal, particularly in regard to the chemical uniformity.

Therefore, the present invention proposes a sampling device which includes a ceramic body for connection to a tube; the body is provided with an inlet duct leading into a mixing chamber, an outlet duct leading from the mixing chamber to a first sample chamber for obtaining a pin-shaped sample, and the first sample chamber is connected to a second sample chamber for obtaining a larger, disk-shaped sample, the inlet duct and the outlet duct each having a port at and into the mixing chamber, the ports being located next to each other, in the lower half of the mixing chamber.

The arrangement and performance of a mixing chamber according to the invention, ensures a complete dissolving of the steel killing agents, even in short filling periods of the sampling apparatus when being submerged into a steel bath. The agent will be uniformly distributed, particularly in the sampling chambers.

DESCRIPTION OF THE DRAWINGS

The present invention will be described in conjunction with the accompanying drawings in which.

Figure 1:
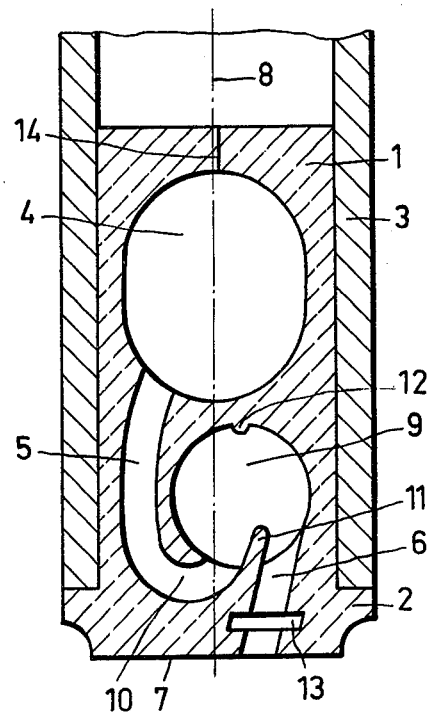
FIG. 1 shows a longitudinal section through the sampling apparatus in the plane of the joint interface of the two half shells part-bodies.

The apparatus of FIG. 1 includes a refractory ceramic body 1 in the form of a half cylinder. The body 1 is inserted into a cardboard tube 3 up to an external stop 2, surrounding body 1. An inlet channel 6 leads from the outwardly extending front surface 7 into the interior of the body. An enlarged portion 13 of the duct 6 contains a de-oxidizing agent for quieting (killing) the steel. The surface 7 is protected by a metal cap (not shown) which can be plugged onto the part of the body 1 projecting from the cardboard tube. This cap is so formed that it will melt after having penetrated slag floating on the metal bath and only thereafter will the inlet channel 6 be opened for the metal to enter.

The inlet channel 6 is arranged off center and obliquely to the longitudinal axis of the body 1, i.e. the channel slopes upwardly and leads into a mixing chamber 9. The mixing chamber 9 may be of disk-shaped or spherical configuration, and the inlet duct charges chamber 9 tangentially.

The mixing chamber 9, in turn, is connected to a duct 10 which, in turn, is connected to a chamber 5, for taking a pin-shaped sample. The sampling chamber 5, terminates in a chamber 4 for taking a disk-shaped sample. The inlet channel 6 has a port leading into the lower half of the mixing chamber 9, and the entrance port of duct 10 is located right next to the entrance port for channel 6. The two ports are separated by a shoulder 11 extending into the mixing chamber 9. A baffle 12 is provided in the upper part of mixing chamber 9. A venting bore 14 is provided in the uppermost point or apex of the disk-shaped sample. Venting bore 14 communicates with the interior of the tube 3.

Figure 2:
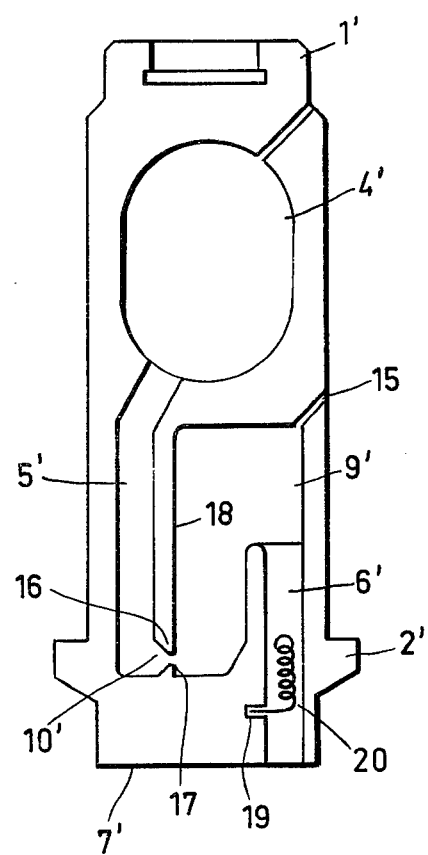
FIG. 2 shows an longitudinal section through a modified embodiment.

In the embodiment of FIG. 2, all the corresponding parts are indicated by similar reference numerals but being further identified by the symbol '.

A mixing chamber 9' has a cylindrical shape and is connected, in sequence, with a duct 5' for a pin-shaped sample and a chamber 4' for a disk-shaped sample. According to the invention, the apparatus is so constructed that the volume of the mixing chamber 9' is at least 1.5 times, preferably, two to three times larger than the volume of the sample cavity 4'. A venting bore 15 is provided in the mixing chamber 9', and in an uppermost position of the chamber during sampling. The duct 10', leading to the chamber 5', is reduced in cross-section. According to a preferred embodiment of the invention, the reduction of the cross-section is obtained by means of a diaphragm-shaped annular, wedge-shaped construction or projection 16, to provide an opening or port, having an internal diameter of 2 to 4 mm. The projection 16 is of such a shape that a wall surface 17 thereof is a portion of the wall 18 of the mixing chamber 9'.

Further, it has been proven to be advantageous to use the smoothing or quieting means for killing the sampled steel in the form of a spirally wounded wire. Preferably, the wire is arranged within the inlet duct or channel 6'. The channel is provided with a side bore 19 for that purpose to receive an outwardly bent off end of the spirally wounded wire 20 for fastening the end thereof to the channel wall. The wire spiral 20 extends otherwise lengthwise in inlet duct 6'.

The apparatus according to the embodiment of FIG. 2 has the advantage that due to the venting bore 15 and due to the reduction of the cross-section of the channel leading from the mixing chamber 5', the latter chamber will be filled first completely with the inflowing metal, the entire content will be killed, and the quieting means will be uniformly distributed in the melt. This way, it is assured that the real sampling cavities or chambers 4' and 5', are already separated from the remaining portion of the sampled material located within the mixing chamber 9'. Therefore, the constriction serves also to establish a braking point and simplifies the preparation of the samples.

What we claim is:

1. Device for sampling molten metal, comprising:
   a ceramic body having a first sampling chamber for obtaining a pin-shaped sample, and a second sampling chamber for obtaining a disk-shaped sample, and connected to the first chamber;
   a mixing chamber in the body;
   inlet duct means in the body leading from the outside into the mixing chamber and having a port in a lower portion thereof; and
   outlet duct means having a port for leading from the mixing chamber adjacent to the port for the inlet duct and also in a lower portion of the mixing chamber, to the first sampling chamber.

2. Device as in claim 1 and, including a shoulder between said ports.

3. Device as in claim 1, said mixing chamber having a circular boundary, the inlet duct leading tangentially into the mixing chamber.

4. Device as in claim 1 or 3, including a baffle projecting into the mixing chamber.

5. Device as in claim 1, said inlet duct provided to receive a steel killing agent.

6. Device as in claim 1, including a venting bore at the uppermost portion of the second chamber.

7. Device as in claim 1, said body having an axis at the inlet duct being oblique to said axis.

8. Device as in claim 1, said mixing chamber being at least one-and-a-half times larger than the second sampling chamber.

9. Device as in claim 8, said mixing chamber being two to three times larger than the second sampling chamber.

10. Device as in claim 1, said outlet duct having a constriction.

11. Device as in claim 1 or 10, said mixing chamber being provided with a venting duct.

12. Device as in claim 1, said inlet duct being provided with a side bore for fastening a wire-shaped steel killing agent.

* * * * *